United States Patent [19]

Krämer et al.

[11] 3,961,061
[45] June 1, 1976

[54] PESTICIDAL 2-AMIDOCARBONYLTHIOBARBITURIC ACIDS

[75] Inventors: Wolfgang Krämer; Wilfried Draber, both of Wuppertal; Ingeborg Hammann, Cologne; Hans Scheinpflug, Leverkusen, all of Germany

[73] Assignee: Bayer Aktiengesellschaft, Leverkusen, Germany

[22] Filed: Feb. 5, 1975

[21] Appl. No.: 547,421

[30] Foreign Application Priority Data
Feb. 7, 1974 Germany............................ 2405733

[52] U.S. Cl. ...................... 424/254; 260/256.5 R; 260/260
[51] Int. Cl.² ................... A01N 9/22; C07D 239/00
[58] Field of Search .................... 260/256.5 R, 260; 424/254

[56] References Cited
UNITED STATES PATENTS

| | | | |
|---|---|---|---|
| 3,636,080 | 1/1972 | Brossi et al. | 260/257 |
| 3,828,043 | 8/1974 | Kay et al. | 260/257 |

OTHER PUBLICATIONS
Chemical Abstracts 66:115663Y (1967).

*Primary Examiner*—Leonard Schenkman
*Attorney, Agent, or Firm*—Burgess, Dinklage & Sprung

[57] ABSTRACT

2-Amidocarbonylthiobarbituric acids of the formula

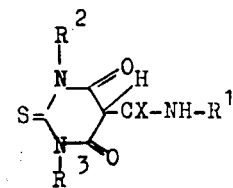

in which
R¹ is alkyl, alkoxyalkyl, alkylthioalkyl, haloalkyl, cycloalkylalkyl, alkenyl, cycloalkyl, cycloalkenyl, haloalkenyl, alkylthiocarbonyl or alkoxycarbonyl, or optionally substituted aryl or aralkyl,
R² and R³ each independently is alkyl, alkenyl, cycloalkyl, aryl, aralkyl or hydrogen, provided that not more than one of R² and R³ is hydrogen, and
X is oxygen or sulfur,
which possess insecticidal, acaricidal, fungicidal and bactericidal properties.

10 Claims, No Drawings

PESTICIDAL 2-AMIDOCARBONYLTHIOBARBITURIC ACIDS

The present invention relates to and has for its objects the provision of particular new 2-amidocarbonylthiobarbituric acids, which possess insecticidal, acaricidal, fungicidal and bactericidal properties, active compositions in the form of mixtures of such compounds with solid and liquid dispersible carrier vehicles, and methods for producing such compounds and for using such compounds in a new way especially for combating pests, e.g. insects, acarids, fungi, and bacteria with other and further objects becoming apparent from a study of the within specification and accompanying examples.

It has been disclosed in German Published Specification DOS No. 2,138,049 that thiobarbituric acid derivatives such as 5-acetyl-3,3-dimethyl-2-thiobarbituric acid (Compound A) have insecticidal, acaricidal, fungicidal and herbicidal properties. However, their activity is not always entirely satisfactory, especially if low amounts and low concentrations are used.

The present invention provides 2-amidocarbonylthiobarbituric acid derivatives, per se or as salts, of the general formula

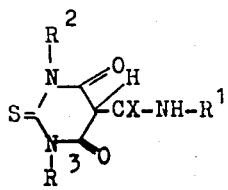

in which
R$^1$ is alkyl, alkoxyalkyl, alkylthioalkyl, haloalkyl, cycloalkylalkyl, alkenyl, cycloalkyl, cycloalkenyl, haloalkenyl, alkylthiocarbonyl or alkoxycarbonyl, or optionally substituted aryl or aralkyl,
R$^2$ and R$^3$ each independently is alkyl, alkenyl, cycloalkyl, aryl, aralkyl or hydrogen, provided that not more than one of R$^2$ and R$^3$ is hydrogen, and
X is oxygen or sulfur.

The compounds can exist in the form shown or as the tautomer, in accordance with the equation

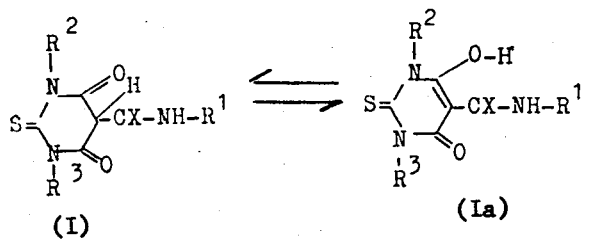

However, for ease of understanding, hereinafter only I will be shown but will be understood to embrace the tautomer or mixtures thereof.

R$^1$ preferably represents straight-chain or branched alkyl with 1 to 12 (especially 1 to 6) carbon atoms; alkoxyalkyl or haloalkyl with 1 to 12 (especially 1 to 6) carbon atoms in the alkyl moiety and 1 to 3 carbon atoms in the alkoxy moiety or 1 to 3 halogen atoms (especially chlorine); alkylthioalkyl with 1 to 6 carbon atoms in the alkyl moiety and 1 to 3 carbon atoms in the alkylthio moiety; alkenyl or haloalkenyl with 2 to 6 carbon atoms and, where relevant, 1 to 3 halogen atoms; optionally methyl-substituted cycloalkyl, cycloalkylalkyl or cycloalkenyl with 5 or 6 (especially 6) carbon atoms in the cycloalkyl or cycloalkenyl radical; optionally substituted aryl or aralkyl with 6 to 10 carbon atoms; or alkoxycarbonyl or alkylthiocarbonyl with 1 to 4 carbon atoms in the alkyl moiety.

Preferred possible substituents, of which one or more may be present, of R$^1$ when it is aryl or aralkyl include halogen (especially fluorine, chlorine or bromine), haloalkyl or haloalkoxy with 1 or 2 carbon atoms and 2 to 5 halogen atoms (especially chlorine and/or fluorine), straight-chain or branched alkyl with 1 to 4 carbon atoms, alkoxy or alkylthio with 1 to 4 carbon atoms, alkylsulfonyl with 1 to 4 carbon atoms and/or the nitro group.

R$^2$ preferably represents straight-chain or branched alkyl with 1 to 6 (especially 1 to 4) carbon atoms, alkenyl with 2 to 6 (especially 2 or 3) carbon atoms, cycloalkyl with 5 to 6 atoms (especially cyclohexyl), or phenyl; while R$^3$ preferably represents straight-chain or branched alkyl with 1 to 6 (especially 1 to 4) carbon atoms, alkenyl with 2 or 3 carbon atoms, cycloalkyl with 5 or 6 carbon atoms (especially cyclohexyl), phenyl, benzyl or hydrogen.

Surprisingly, the amidocarbonylthiobarbituric acid derivatives and salts thereof according to the invention display a substantially greater insecticidal, acaricidal and fungicidal action than the thioburbituric acid derivatives, such as, for example, 5-acetyl-1,3-dimethyl-2-thiobarbituric acid, which are known in the art. They thus represent a genuine enrichment of the art.

The invention also provides a process for the production of a compound of the invention in which a thiobarbituric acid of the general formula

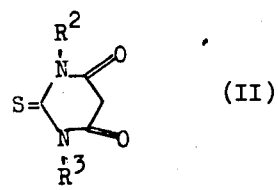

in which
R$^2$ and R$^3$ have the abovementioned meanings, is reacted with an isocyanate or isothiocyanate of the general formula $$XCN-R^1 \qquad (III)$$

in which
R$^1$ and X have the abovementioned meanings, optionally in the presence of an acid acceptor and/or a solvent and optionally at a temperature of 10° to 150°C.

If 1,3-dimethyl-2-thiobarbituric acid and 4-chlorophenyl isocyanate are used as starting materials, the course of the reaction can be represented by the following equation:

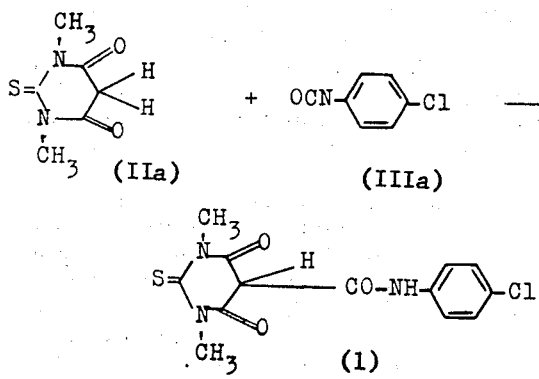

Thiobarbituric acids of the formula II are already known. As examples there may be mentioned: 1,3-dimethyl-2-thiobarbituric acid, 1-methyl-2-thiobarbituric acid, 3-ethyl-1-methyl-2-thiobarbituric acid, 3-isopropyl-1-methyl-2-thiobarbituric acid, 1-methyl-3-propyl-2-thiobarbituric acid, 3-butyl-1-methyl-2-thiobarbituric acid, 3-i-butyl-1-methyl-2-thiobarbituric acid, 3-s-butyl-1-methyl-2-thiobarbituric acid, 3-t-butyl-1-methyl-2-thiobarbituric acid, 1,3-dicyclohexyl-2-thiobarbituric acid, 1,3-diphenyl-2-thiobarbituric acid, 3-benzyl-1-methyl-2-thiobarbituric acid and 3-allyl-1-methyl-2-thiobarbituric acid.

Isocyanates or isothiocyanates of formula III are already known and can be prepared according to customary methods by reacting about one mol of the corresponding amine with about one mole of phosgene or thiophosgene preferably in the presence of an inert organic solvent at elevated temperatures as described in Houben Weyl Methoden der organischen Chemie Vol. VIII (1952). The isothtiocyanates can be prepared according to customary methods by reacting the corresponding thioureas with acids. The following may be mentioned as examples: 4-methylsulfonylphenyl isocyanate, 4-methoxyphenyl isocyanate, 4-ethoxyphenyl isocyanate, 3-chlorophenyl isocyanate, 3-bromophenyl isocyanate, 3-fluorophenyl isocyanate, 4-bromophenyl isocyanate, 4-fluorophenyl isocyanate, 4-chlorophenyl isocyanate, 4-methyl-phenyl isocyanate, 4-tertiary butylphenyl isocyanate, 4-nitrophenyl isocyanate, 4-trifluoromethylphenyl isocyanate, 3-trifluoromethylphenyl isocyanate, 3-methylphenyl isocyanate, 2-chlorophenyl isocyanate, 2-methylphenyl isocyanate, 2-methoxyphenyl isocyanate, 3,4-dichlorophenyl isocyanate, 3-chloro-2-methylphenyl isocyanate, 2-chloro-4-nitrophenyl isocyanate, 4-chloro-2-methylphenyl isocyanate, 4-chloro-3-methylphenyl isocyanate, 4-chloro-3-trifluoromethylphenyl isocyanate, 3-chloro-4-trifluoromethylphenyl isocyanate, 2-chloro-4-trifluoromethylphenyl isocyanate, 2-chloro-4-chlorodifluoromethylphenyl isocyanate, 3-chloro-4-trifluoromethoxyphenyl isocyanate, 2,4,6-trichlorophenyl isocyanate, 2,6-dichloro-4-trifluoromethylphenyl isocyanate, 4-bromo-2-isopropylphenyl isocyanate, 4-bromo-2,6-diethylphenyl isocyanate, 2,6-diisopropyl-4-nitrophenyl isocyanate, α-naphthylisocyanate, methyl isocyanate, methyl isothiocyanate, ethyl isothiocyanate, n-butyl isocyanate, t-butyl isocyanate, propyl isocyanate, propyl isothiocyanate, i-propyl isocyanate, allyl isocyanate, 2-methoxyethyl isocyanate, cyclohexyl isocyanate, cyclohexyl isothiocyanate, 2-methylcyclohexyl isocyanate, 4-methylcyclohexyl isocyanate, cyclohexylmethyl isocyanate, 6-chlorohexyl isocyanate, 2-chloroethyl isocyanate, 4-chloro-but-2-enyl isocyanate, but-2-enyl isocyanate, 1-methoxypropyl isocyanate and 1-chloromethylprop-2-enyl isocyanate.

For many purposes, the amidocarbonylthiobarbituric acids according to the invention can be employed in the form of salts with physiologically tolerated bases, for example, triethylamine salts, ammonium salts, sodium salts and potassium salts.

The solvent which may be used in the process according to the invention may for example by any inert organic solvent. Preferred examples include hydrocarbons such as ligroin, petroleum ether, benzene, toluene and xylene, chlorinated hydrocarbons such as chloroform, carbon tetrachloride, ethylene chloride or methylene chloride, or ketones such as acetone and methyl ethyl ketone, and ethers, such as diethyl ether, diisopropyl ether, diisobutyl ether, dibutyl ether, tetrahydrofuran and dioxane.

Any of the usual acid-binding agents can be used as the acid acceptor. Alkali metal hydroxides, alkaline earth metal hydroxides, alkali metal carbonates, alkaline earth metal carbonates and organic bases may be mentioned as preferred examples. Tertiary organic bases, for example triethylamine, pyridine, dimethylcyclohexylamine and dimethylbenzylamine, and inorganic acid-binding agents, for example sodium bicarbonate and potassium bicarbonate, are particularly suitable.

The reaction temperatures can be varied within a wide range. In general, the reaction is carried out at 10° to 150°C, preferably 20° to 100°C. It is generally carried out under normal pressure.

In carrying out the process according to the invention, 1 mole of isocyanate of the formula (III) and, where appropriate, 1 to 1.2 moles of inorganic acid acceptor or 0.1 to 1 mole of organic acid acceptor, are generally employed per mole of thiobarbituric acid. Exceeding this stated amount produces no significant improvement in yield.

To isolate the product, the solvent may be distilled off, the residue taken up in water, the solution acidified and the undissolved matter filtered off. The filtrate may be discarded. The residue may be washed well with alcohol, dried and optionally purified by recrystallization.

As has already been mentioned, the active compounds according to the invention are distinguished by an excellent insecticidal and acaricidal activity against plant pests and hygiene pests. They have a good action against sucking insects and also against biting insects and mites (Acarina). For this reason, the compounds according to the invention are employed successfully as pesticides in plant protection.

To the sucking insects there belong, in the main, aphids (Aphididae) such as the green peach aphid (*Myzus persicae*), the bean aphid (*Doaralis fabae*), the bird cherry aphid (*Rhopalosiphum padi*), the pea aphid (Macrosiphum pisi) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly caterpillars (Lepidoptera) such as the diamond-back moth (*Plutella maculipennis*), the gypsy moth (*Lymantria dispar*), the browntail moth (*Euproctis cryssorrhoea*) *and tent caterpillar* (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kühniella*) and greater wax moth (*Galleria mellonella*).

Also to be classed with the biting insects are beetles (Coleoptera), for example the granary weevil (*Sitophilus granarius = Calandra granaria*), the Colordao beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius = Acanthoscelides obtectus*), the leather beetle (*Dermestes frischi*), the khapra beetle (*Trogoderma granarium*), the flour beetle (*Tribolium castaneum*), the northern corn billbug (*Calandra* or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes spec.*) and larvae of the cockchafer (*Melolontha melolontha*); cockroaches, such as the German cockroach (*Blattella germanica*), American cockroach (*Periplaneta americana*), Madeira cockroach (*Leucophaea* or *Rhyparobia maderae*), oriental cockroach (*Blatta orientalis*), the giant cockroach (*Blaberus giganteus*) and the black giant cockroacch (*Blaberus fuscus*) as well as Henschoutedenia flexivitta; further, Orthtoptera, for example the house cricket (*Gryrllus domesticus*); termites such as the eastern subterranean termite (*Reticulitermes flavipes*) and Hymenoptera such as ants, for example the graden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern hous mosquito (*Culex pipiens*) and the malaria mosquito (*Anopheles stephensi*).

With the mites (Acari) there are classed, in particular, the spider mites (Tetranychidae) such as the twospotted sipder mite (*Tetranychus urticae*) and the European red mite (*Paratetranychus pilosus = Panonychus ulmi*), gall mites, for example the blackcurrant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

The active compounds according to the invention furthermore display strong fungitoxic and bacteriotoxic action. They do not harm crop plants in the concentrations required to combat fungi and bacteria, and have a low toxicity to warm-blooded animals. For these reasons, they are suitable for use as plant protection agents for combating fungi and bacteria. Fungitoxic agents are employed in plant protection for combating *Archimycetes, Phycomycetes, Ascomycetes, Basidiomycetes* and *Fungi Imperfecti*.

The compounds according to the invention are active against fungi and bacteria which attack various crop plants, for example species of *Pythium*, species of *Phytophthora*, species of Fusarium, *Verticillium alboatrum, Phialophora cinerescens, Sclerotinia sclerotiorum*, species of *Botrytis, Cochliobolus miyabeanus, Mycosphaerella musicola, Cercospora personata, Helminthosporium gramineum*, species of Alternaria, species of *Colletotrichum, Venturia inaequalis*, species of *Rhizoctonia, Thielaviopsis basicola* and the bacterium *Xanthomonas oryzae*. The compounds according to the invention are also active against diseases of cereals, for example *Puccinia recondita, Erysiphe graminis* and *Tilletia caries*.

Furthermore, the active compounds according to the invention display a very good molluscicidal activity.

The active compounds according to the invention also have a very good activity against animal ectoparasites, such as ticks, as well as against endoparasites.

The active compounds according to the instant invention can be utilized, if desired, in the form of the usual formulations or compositions with conventional inert (i.e. plant compatible or herbicidally inert) pesticide diluents or extenders, i.e., diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g., conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhur, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, acaricides, fungicides, bactericides and molluscicides, or nematocides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commerically marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects, acarids, fungi and bacteria which comprises applying to at least one of correspondingly (a) such insects, (b) such acarids, (c) such fungi, (d) such bacteria, and (e) the corresponding habitat thereof, i.e. the locus to be protected, e.g. to a growing crop, to an area where a crop is to be grown or to a domestic animal, a correspondingly combative or toxic amount, i.e. an insecticidally, acaricidally, fungicidally or bactericidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

Example 1

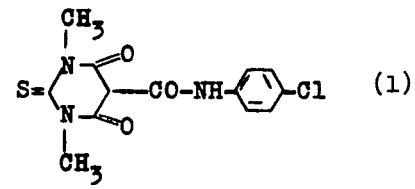

8.6 g (0.05 mole) of 1,3-dimethyl-2-thiobarbituric acid were dissolved in 200 ml of benzene and 5.0 g (0.05 mole) of triethylamine were added thereto at room temperature. The solution was warmed to 35° – 40°C and slowly added dropwise, with stirring and reflux cooling, to 7.7 g (0.05 mole) of 4-chlorophenyl isocyanate. After heating for 15 hours under refulx, the mixture was cooled and acidified with 10 ml of concentrated hydrochloric acid. The solvent was distilled off in vacuo. The residue was taken up in 200 ml of water, whereupon triethylammonium chloride dissolved. The undissolved matter was filtered off, rinsed twice with 50 ml of methanol and dried.

13.5 g (83% of theory) of 5-(4'-chloro-1'-anilido)-carbonyl-1,3-dimethyl-2-thiobarbituric acid of melting point 243° – 245°C were obtained.

The compounds shown in Table I which follows were prepared analogously:

Table 1

$$S=\begin{array}{c}R^2\\|\\N\\\end{array}\begin{array}{c}O\\\|\\-CX-NH-R^1\\\|\\O\end{array}\begin{array}{c}\\N\\|\\R^3\end{array}$$

| Compound No. | R¹ | R² | R³ | X | Melting point, °C |
|---|---|---|---|---|---|
| 2 | Cl-C₆H₄- (2-Cl) | CH₃ | CH₃ | O | 165–167 |
| 3 | Cl-C₆H₄- (4-Cl) | CH₃ | C₂H₅ | O | 183–184 |
| 4 | Cl-C₆H₄- (4-Cl) | CH₃ | CH(CH₃)₂ | O | 179–180 |
| 5 | Cl-C₆H₄- (4-Cl) | CH₃ | H | O | 274–275 |
| 6 | Cl-C₆H₄- (2-Cl) | CH₃ | CH(CH₃)₂ | O | 136–137 |
| 7 | Cl-C₆H₄- (2-Cl) | CH₃ | H | O | 278 |
| 8 | Cl-C₆H₄- (3-Cl) | CH₃ | C₂H₅ | O | 148 |
| 9 | C₆H₅- | CH₃ | CH₃ | O | 203–204 |
| 10 | C₆H₅- | CH₃ | C₂H₅ | O | 174–176 |
| 11 | C₆H₅- | CH₃ | CH(CH₃)₂ | O | 192 |
| 12 | C₆H₅- | CH₃ | H | O | 274 |
| 13 | NO₂-C₆H₄- | CH₃ | CH₃ | O | 224–225 |
| 14 | NO₂-C₆H₄- | CH₃ | C₂H₅ | O | 179–180 |
| 15 | CH₃-C₆H₄- | CH₃ | CH₃ | O | 160–162 |
| 16 | (CH₃)₃C-C₆H₄- | CH₃ | CH₃ | O | 175–178 |
| 17 | C₂H₅O-C₆H₄- | CH₃ | CH₃ | O | 180 |
| 18 | CF₃-C₆H₄- | CH₃ | CH₃ | O | 162–165 Triethylammonium salt 140–143 |
| 19 | CF₃-C₆H₄- | CH₃ | C₂H₅ | O | 155 |
| 20 | CF₃-C₆H₄- | CH₃ | CH(CH₃)₂ | O | 128–130 |
| 21 | CF₃-C₆H₄- | CH₃ | H | O | 256–257 |

Table 1-continued

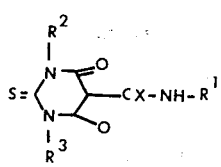

| Compound No. | R¹ | R² | R³ | X | Melting point, °C |
|---|---|---|---|---|---|
| 22 | Cl,Cl-phenyl (2,3-diCl) | $CH_3$ | $CH_3$ | O | 218–220 |
| 23 | Cl,Cl-phenyl | $CH_3$ | $CH_3CH_2-$ | O | 150–154 |
| 24 | Cl,Cl-phenyl | $CH_3$ | $CH(CH_3)_2$ | O | 194–195 |
| 25 | Cl,Cl-phenyl | $CH_3$ | H | O | 272 |
| 26 | Cl,Cl-phenyl | $CH_3$ | $CH_3$ | O | 214–215 |
| 27 | $CH_3$,Cl-phenyl | $CH_3$ | $CH_3$ | O | 190–194 |
| 28 | $CH_3$,Cl-phenyl | $CH_3$ | $CH(CH_3)_2$ | O | 170–172 |
| 29 | $CH_3$,Cl-phenyl | $CH_3$ | H | O | 290 |
| 30 | $CH_3$,Cl-phenyl | $CH_3$ | $C_2H_5$ | O | 140–141 |
| 31 | Cl,$CH_3$-phenyl | $CH_3$ | $CH_3$ | O | 206–207 |
| 32 | Cl,$CH_3$-phenyl | $CH_3$ | $CH(CH_3)_2$ | O | 194–196 |
| 33 | Cl,$CH_3$-phenyl | $CH_3$ | $C_2H_5$ | O | 151–152 |
| 34 | Cl,$CH_3$-phenyl | $CH_3$ | H | O | 247–248 |
| 35 | $CF_3$,Cl-phenyl | $CH_3$ | $CH_3$ | O | 196–197 |

Table 1-continued
| Compound No. | R¹ | R² | R³ | X | Melting point, °C |
|---|---|---|---|---|---|
| 36 |  | CH₃ | C2H₅ | O | 150–152 |
| 37 |  | CH₃ | CH(CH₃)₂ | O | 164–165 |
| 38 |  | CH₃ | CH₃ | O | 185 |
| 39 |  | CH₃ | C₂H₅ | O | 150 |
| 40 |  | CH₃ | CH(CH₃)₂ | O | 134–137 |
| 41 |  | CH₃ | CH₃ | O | 168–169 |
| 42 |  | CH₃ | C₂H₅ | O | 145–146 |
| 43 |  | CH₃ | CH(CH₃)₂ | O | 134–135 |
| 44 |  | CH₃ | CH₃ | O | 148–152 |
| 45 |  | CH₃ | H | O | 212 |
| 46 |  | CH₃ | CH(CH₃)₂ | O | 120–121 |
| 47 |  | CH₃ | C₂H₅ | O | 144–145 |
| 48 |  | CH₃ | CH₃ | O | 157–158 |
| 49 |  | CH₃ | CH(CH₃)₂ | 0 | 114–115 |
| 50 |  | CH₃ | C₂H₅ | O | 136–137 |

Table 1-continued

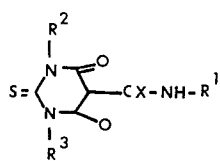

| Compound No. | R¹ | R² | R³ | X | Melting point, °C |
|---|---|---|---|---|---|
| 51 | Cl,Cl,Cl-phenyl (2,4,6-tri) | $CH_3$ | $C_2H_5$ | O | 138–140 |
| 52 | $CF_3$-, Cl, Cl-phenyl | $CH_3$ | $CH_3$ | O | 165–166 |
| 53 | $CF_3$-, Cl, Cl-phenyl | $CH_3$ | $C_2H_5$ | O | 128–130 |
| 54 | $CF_3$-, Cl, Cl-phenyl | $CH_3$ | $CH(CH_3)_2$ | O | 140–142 |
| 55 | Br-, $CH(CH_3)_2$-phenyl | $CH_3$ | $CH_3$ | O | 173–174 |
| 56 | Br-, $C_2H_5$, $C_2H_5$-phenyl | $CH_3$ | $CH_3$ | O | 200 |
| 57 | Br-, $CH(CH_3)_2$, $CH(CH_3)_2$-phenyl | $CH_3$ | $CH_3$ | O | 225 |
| 58 | $NO_2$-, $CH(CH_3)_2$, $CH(CH_3)_2$-phenyl | $CH_3$ | $CH_3$ | O | 259–261 |
| 59 | cyclohexyl (H) | $CH_3$ | $CH_3$ | O | 174–175 |
| 60 | cyclohexyl (H) | $CH_3$ | $C_2H_5$ | O | 113–114 |
| 61 | cyclohexyl (H) | $CH_3$ | $CH(CH_3)_2$ | O | 118–119 |
| 62 | naphthyl | $CH_3$ | $CH_3$ | O | 259–260 |
| 63 | $CH_3$ | $CH_3$ | $CH_3$ | O | 162 |
| 64 | $CH_3$ | $CH_3$ | $CH_3$ | S | 168–169 |
| 65 | $CH_3$ | $CH_3$ | $CH(CH_3)_2$ | O | 122 |
| 66 | $CH_3$ | $CH_3$ | $C_2H_5$ | O | 114–115 |
| 67 | $CH_3$ | $CH_3$ | H | O | 277 |
| 68 | $C_2H_5$ | $CH_3$ | $CH_3$ | O | 91–94 |
| 69 | $C_2H_5$ | $CH_3$ | $C_2H_5$ | O | 75–78 |
| 70 | $C_2H_5$ | $CH_3$ | $CH(CH_3)_2$ | O | 80–81 |
| 71 | $C_2H_5$ | $CH_3$ | H | O | 204–205 |

Table 1-continued

[Structure: S=C with N-R² and N-R³ in ring, two C=O groups, and -CX-NH-R¹ substituent]

| Compound No. | R¹ | R² | R³ | X | Melting point, °C |
|---|---|---|---|---|---|
| 72 | $C_3H_7$ | $CH_3$ | $CH_3$ | O | 80–82 |
| 73 | $C_3H_7$ | $CH_3$ | $CH(CH_3)_2$ | O | 69–72 |
| 74 | $C_3H_7$ | $CH_3$ | H | O | 167 |
| 75 | $CH(CH_3)_2$ | $CH_3$ | $CH_3$ | O | 115 |
| 76 | $C_4H_9$ | $CH_3$ | $CH_3$ | O | 72 |
| 77 | $C_4H_9$ | $CH_3$ | $CH(CH_3)_2$ | O | 62–64 |
| 78 | $C(CH_3)_3$ | $CH_3$ | $CH_3$ | O | 154–155 |
| 79 | $C(CH_3)_3$ | $CH_3$ | $CH(CH_3)_2$ | O | 87–92 |
| 80 | $CH_2-CH=CH_2$ | $CH_3$ | $CH_3$ | S | 125–126 |
| 81 | $CH_2-CH=CH_2$ | $CH_3$ | $CH(CH_3)_2$ | S | 121–123 |
| 82 | $-(CH_2)_3OCH_3$ | $CH_3$ | $CH_3$ | O | 80–81 |
| 83 | $-COSC_4H_9$ | $CH_3$ | $CH_3$ | O | 94–96 |
| 84 | $-COSC_4H_9$ | $CH_3$ | $CH(CH_3)_2$ | O | 94–97 |
| 85 | $C_5H_{10}CH_2Cl$ | $CH_3$ | $CH_3$ | O | 55–56 |
| 86 | $CH_3$ | $CH(CH_3)_2$ | $CH_3$ | S | 103–105 |
| 87 | $C(CH_3)_3$ | $CH_3$ | H | O | 208–210 |
| 88 | cyclohexyl-CH₃ | $CH_3$ | $CH_3$ | O | 121 |
| 89 | 4-methylcyclohexyl | $CH_3$ | $CH_3$ | O | 123 |
| 90 | 3-methylphenyl | $C_2H_5$ | $CH_3$ | O | 157–58 |
| 91 | $-CH_2-$cyclohexyl | $CH_3$ | $CH_3$ | O | 100–102 |
| 92 | $C_4H_9$ | $CH_3$ | $C_2H_5$ | O | 48 |
| 93 | 4-chlorophenyl | $CH_3$ | $C_3H_7$ | O | 158 |
| 94 | 4-chlorophenyl | $CH_3$ | $-CH_2-$phenyl | O | 174 |
| 95 | 3-chlorophenyl | $CH_3$ | $C_3H_7$ | O | 148 |
| 96 | 3-chlorophenyl | $CH_3$ | $-CH_2-$phenyl | O | 158–160 |
| 97 | 4-methylphenyl | $CH_3$ | $C_2H_5$ | O | 114–115 |
| 98 | 2-methyl-4-chlorophenyl | $CH_3$ | $C_3H_7$ | O | 160–163 |
| 99 | 2-methyl-4-chlorophenyl | $CH_3$ | $CH_2-$phenyl | O | 213–214 |
| 100 | 3,4-dichlorophenyl | $CH_3$ | $C_2H_5$ | O | 177–178 |
| 101 | 2-chloro-3-methylphenyl | $CH_3$ | $CH_3$ | O | 238–239 |

Table 1-continued

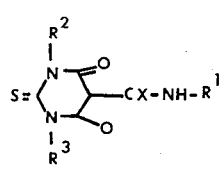

| Compound No. | R¹ | R² | R³ | X | Melting point, °C |
|---|---|---|---|---|---|
| 102 | cyclohexyl | $CH_3$ | $CH_2$–phenyl | O | 110 |
| 103 | 2-Cl, 4-$CF_3$-phenyl | $C_6H_5$ | $C_6H_5$ | O | 223–4°C |
| 104 | $-(CH_2)_5CH_2Cl$ | $CH_3$ | H | O | 143 |
| 105 | 4-Cl-phenyl | $CH_2-CH=CH_2$ | H | O | Triethylammonium salt 134 |
| 106 | $C_2H_5$ | $CH_2-CH=CH_2$ | H | O | 194 |
| 107 | 2-Cl-phenyl | $CH_3$ | $CH_3$ | O | 218 |
| 108 | 4-Br-phenyl | $CH_3$ | $CH_3$ | O | 164 |
| 109 | 2-Cl, 4-$NO_2$-phenyl | $CH_3$ | $CH_3$ | O | 185 |
| 110 | $(CH_2)_{11}CH_3$ | $CH_3$ | $CH_3$ | O | 48 |
| 111 | $-CH_2$–phenyl | $CH_3$ | $CH_3$ | O | 142 |
| 112 | 2-Cl-phenyl | $CH_3$ | $C_2H_5$ | O | 163–4 |
| 113 | 3-Br-phenyl | $CH_3$ | $C_2H_5$ | O | 173 |
| 114 | 4-F-phenyl | $CH_3$ | $C_2H_5$ | O | 157–8 |
| 115 | 4-$CH_3$-phenyl | $CH_3$ | $C_2H_5$ | O | 174 |
| 116 | 2-$OCH_3$-phenyl | $CH_3$ | $C_2H_5$ | O | 191 |
| 117 | 4-$NO_2$-phenyl | $CH_3$ | $C_2H_5$ | O | 179 |
| 118 | 4-$SO_2CH_3$-phenyl | $CH_3$ | $C_2H_5$ | O | 218 |

Table 1-continued
| Compound No. | R¹ | R² | R³ | X | Melting point, °C |
|---|---|---|---|---|---|
| 119 | 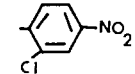 | CH₃ | C₂H₅ | O | 180 |
| 120 | 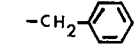 | CH₃ | C₂H₅ | O | 249 |
| 121 | i-C₃H₇ | CH₃ | C₂H₅ | O | 87 |
| 122 | (CH₂)₁₁CH₃ | CH₃ | C₂H₅ | O | 40 |
| 123 | -CH₂- | CH₃ | C₂H₅ | O | 108 |
| 124 | 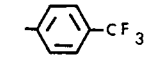 | CH₃ | C₃H₇ | O | 162 |
| 125 |  | CH₃ | C₃H₇ | O | 87 |
| 126 |  | CH₃ | C₃H₇ | O | 174 |
| 127 |  | CH₃ | C₃H₇ | O | 137 |
| 128 |  | CH₃ | C₃H₇ | O | 124 |
| 129 |  | CH₃ | C₃H₇ | O | 140 |
| 130 |  | CH₃ | C₃H₇ | O | 162 |
| 131 |  | CH₃ | C₃H₇ | O | 129 |
| 132 |  | CH₃ | C₃H₇ | O | 105 |
| 133 | CH₃ | CH₃ | C₃H₇ | O | 89 |
| 134 | C₂H₅ | CH₃ | C₃H₇ | O | 82 |
| 135 | C₃H₇ | CH₃ | C₃H₇ | O | 70 |
| 136 | i-C₃H₇ | CH₃ | C₃H₇ | O | 77 |
| 137 | C₄H₉ | CH₃ | C₃H₇ | O | 41 |
| 138 | —C₅H₁₀CH₂Cl | CH₃ | C₃H₇ | O | 57 |
| 139 |  | CH₃ | C₃H₇ | O | 80 |
| 140 | -Cl | CH₃ | CH₂—CH=CH₂ | O | 134 |

Table 1-continued

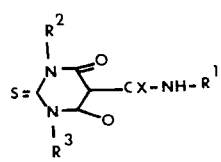

| Compound No. | R¹ | R² | R³ | X | Melting point, °C |
|---|---|---|---|---|---|
| 141 | $C_2H_5$ | $CH_3$ | $CH_2-CH=CH_2$ | O | 79 |
| 142 | phenyl | $C_2H_5$ | $C_2H_5$ | O | 182 |
| 143 | 4-Cl-phenyl | $C_2H_5$ | $C_2H_5$ | O | 178 |
| 144 | 3-Cl-phenyl | $C_2H_5$ | $C_2H_5$ | O | 149 |
| 145 | 4-$NO_2$-phenyl | $C_2H_5$ | $C_2H_5$ | O | 176 |
| 146 | 4-$CF_3$-phenyl | $C_2H_5$ | $C_2H_5$ | O | 158 |
| 147 | 2,3-di-Cl-phenyl | $C_2H_5$ | $C_2H_5$ | O | 159 |
| 148 | 2-$CH_3$-4-Cl-phenyl | $C_2H_5$ | $C_2H_5$ | O | 180 |
| 149 | 2-Cl-4-$CF_3$-phenyl | $C_2H_5$ | $C_2H_5$ | O | 162 |
| 150 | 2-Cl-4-$CF_3$-phenyl | $C_2H_5$ | $C_2H_5$ | O | 182 |
| 151 | 2-Cl-4-$OCF_3$-phenyl | $C_2H_5$ | $C_2H_5$ | O | 172 |
| 152 | 2,4,6-tri-Cl-phenyl | $C_2H_5$ | $C_2H_5$ | O | 117 |
| 153 | 3,4-di-Cl-5-$CF_3$-phenyl | $C_2H_5$ | $C_2H_5$ | O | 191 |
| 154 | $CH_3$ | $C_2H_5$ | $C_2H_5$ | O | 112 |
| 155 | $C_2H_5$ | $C_2H_5$ | $C_2H_5$ | O | 113 |
| 156 | $C_3H_7$ | $C_2H_5$ | $C_2H_5$ | O | 48 |
| 157 | $-CH(CH_3)_2$ | $C_2H_5$ | $C_2H_5$ | O | 78 |
| 158 | $C_4H_9$ | $C_2H_5$ | $C_2H_5$ | O | 167 |
| 159 | $-C(CH_3)_3$ | $C_2H_5$ | $C_2H_5$ | O | 93 |

Table 1-continued

| Compound No. | R¹ | R² | R³ | X | Melting point, °C |
|---|---|---|---|---|---|
| 160 | (cyclohexyl)-H | $C_2H_5$ | $C_2H_5$ | O | 134 |
| 161 | —$CH_3$ | $C_4H_9$ | $C_4H_9$ | O | 94 |
| 162 | (phenyl)-Cl | $C_4H_9$ | $C_4H_9$ | O | 120 |
| 163 | (phenyl) | (phenyl)-Cl, $CH_3$ | $CH_3$ | O | 211 |
| 164 | (phenyl)-$CF_3$ | (phenyl)-Cl, $CH_3$ | $CH_3$ | O | 136 |
| 165 | (phenyl)-$CF_3$ | (phenyl)-Cl, $CH_3$ | $CH_3$ | O | 132 |
| 166 | (phenyl)-Cl | (phenyl)-Cl, $CH_3$ | $CH_3$ | O | 210 |
| 167 | (phenyl) | —$CH_2$-(phenyl) | $CH_3$ | O | 185 |
| 168 | (phenyl)-$CF_3$ | —$CH_2$-(phenyl) | $CH_3$ | O | 147 |
| 169 | $CH_3$ | —$CH_2$-(phenyl) | $CH_3$ | O | 125 |
| 170 | $C_2H_5$ | —$CH_2$-(phenyl) | $CH_3$ | O | 112 |
| 171 | $C_3H_7$ | —$CH_2$-(phenyl) | $CH_3$ | O | 95 |
| 172 | —CH($CH_3$)$_2$ | —$CH_2$-(phenyl) | $CH_3$ | O | 128 |
| 173 | $C_5H_{10}CH_2Cl$ | —$CH_2$-(phenyl) | $CH_3$ | O | 68 |
| 174 | (phenyl)-$CH_3$, Cl | (phenyl) | (phenyl) | O | 243 |
| 175 | $C_2H_5$ | (phenyl) | (phenyl) | O | 189 |
| 176 | —CH($CH_3$)$_2$ | (phenyl) | (phenyl) | O | 236 |

Table 1-continued

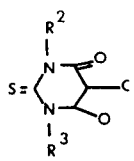

| Compound No. | R¹ | R² | R³ | X | Melting point, °C |
|---|---|---|---|---|---|
| 177 | —C₄H₉ | phenyl | phenyl | O | 204 |

Other compounds which can be similarly prepared include:

| Compound No. | R¹ | R² | R³ | X |
|---|---|---|---|---|
| 178 | 3-(SCH₃)C₆H₄—C₂H₄— | C₆H₅—C₂H₄— | CH₃ | S |
| 179 | C₂H₅—S—C₂H₄— | CH₃ | CH₂=CH—CH₂— | O |
| 180 | cyclopentenyl | cyclohexyl | cyclohexyl | O |
| 181 | ClCH=CH— | CH₃ | CH₃ | S |
| 182 | C₂H₅OCO— | 4-Cl-C₆H₄—CH₂— | H | S | and the like.

Example 2

Phaedon larvae test
Solvent: 3 parts by weight of diemthylformamide
Emuslifier; 1 part by weight of alkylarly polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) were sprayed with the preparation of the active compound until dripping wet and were then infested with mustard beetle larvae (*Phaedon cochleariae*).

After the specified periods of time, the degree of destruction was determined in %: 100% means that all beetle larvae were killed whereas 0% means that none of the beetle larvae were killed.

The active compounds, the concentrations of the active compounds, the evaluation times and the results can be seen from Table 2.

Table 2

(insects which damage plants)
Phaedon larvae test

| Active compounds | Active compound concentration in % by weight | Degree of destruction in % after 3 days |
|---|---|---|
| (known) (A) | 0.1 | 100 |
|  | 0.01 | 0 |
| (12) | 0.1 | 100 |
|  | 0.01 | 100 |
| (21) | 0.1 | 100 |
|  | 0.01 | 100 |
| (5) | 0.1 | 100 |
|  | 0.01 | 100 |
| (31) | 0.1 | 100 |
|  | 0.01 | 95 |
| (27) | 0.1 | 100 |
|  | 0.01 | 95 |
| (18) | 0.1 | 100 |

Table 2-continued

| Active compounds | (insects which damage plants) Phaedon larvae test | |
|---|---|---|
| | Active compound concentration in % by weight | Degree of destruction in % after 3 days |
| (18) | 0.01 | 100 |
| | 0.1 | 100 |
| Triethylammonium salt (41) | 0.1 | 100 |
| | 0.1 | 100 |
| | 0.01 | 100 |
| (38) | 0.1 | 100 |
| | 0.01 | 100 |
| (35) | 0.1 | 100 |
| | 0.01 | 100 |
| (52) | 0.1 | 100 |
| | 0.01 | 100 |
| (2) | 0.1 | 100 |
| | 0.01 | 100 |
| (22) | 0.1 | 100 |
| | 0.01 | 90 |
| (33) | 0.1 | 100 |
| | 0.01 | 100 |
| (30) | 0.1 | 100 |
| | 0.01 | 100 |
| (19) | 0.1 | 100 |
| | 0.01 | 100 |
| (42) | 0.1 | 100 |
| | 0.01 | 90 |
| (39) | 0.1 | 100 |
| | 0.01 | 80 |
| (8) | 0.1 | 100 |
| | 0.01 | 100 |
| (3) | 0.1 | 100 |
| | 0.01 | 100 |
| (23) | 0.1 | 100 |
| | 0.01 | 100 |
| (51) | 0.1 | 100 |
| | 0.01 | 100 |
| (6) | 0.1 | 100 |
| | 0.01 | 100 |
| (48) | 0.1 | 100 |
| | 0.01 | 100 |
| (50) | 0.1 | 100 |
| | 0.01 | 90 |

Example 3

Tetranychus test (resistant)
Solvent: 3 parts by weight of dimethylformamide
Emulsifier: 1 part by weight of alkylarly polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10 – 30 cm, were sprayed with the preparation of the active compound until dripping wet. These bean plants were heavily infested with the common or twospotted spider mite (*Tetranychus urticae*) in all stages of development.

After the specified periods of time, the effectiveness of the preparation of active compound was determined by counting the dead mites. The degree of destruction thus obtained is expressed as a percentage: 100% means that all the spider mites were killed whereas 0% means that none of the spider mites were killed.

The active compounds, the concentrations of the active compounds, the evaluation times and the results can be seen from Table 3.

Table 3

| Active compounds | (mites which damage plants) Tetranychus test | |
|---|---|---|
| | Active compound concentration in % by weight | Degree of destruction in % after 2 days |

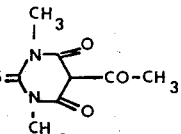

| | | |
|---|---|---|
| (known) (A) (63) | 0.1 | 40 |
| | 0.01 | 0 |
| (60) | 0.1 | 100 |
| | 0.1 | 90 |

Example 4

Mycelium growth test
Nutrient medium used:
20 parts by weight of agar-agar
200 parts by weight of potato decoction
5 parts by weight of malt
15 parts by weight of dextrose
5 parts by weight of peptone
2 parts by weight of $Na_2HPO_4$
0.3 part by weight of $Ca(NO_3)_2$
Ratio of solvent mixture to nutrient medium:
2 parts by weight of solvent mixture
100 parts by weight of agar nutrient medium
Composition of solvent mixture:
0.19 part by weight of acetone
0.01 part by weight of alkylarly polyglycol ether emulsifier
1.80 parts by weight of water The amount of active compound required for the desired concentration of active compound in the nutrient medium was mixed with the stated amount of the solvent mixture. The concentrate was thoroughly mixed, in the stated proportion, with the liquid nutrient medium which had been cooled to 42°C, and was poured into Petri dishes of 9 cm diameter. Control plates to which the preparation had not been added were also set up.

When the nutrient medium had cooled and solidified, the plates were inoculated with the species of pest stated in the table and incubated at about 21°C.

Evaluation was carried out after 4 to 10 days dependent on the speed of growth of the pest. When evaluation was carried out the radial growth of the mycelium on the treated nutrient medium was compared with the growth on the control nutrient medium. In the evaluation of the pest growth, the following characteristic values were used:

1 no pest growth
up to 3 very strong inhibition of growth
up to 5 medium inhibition of growth
up to 7 slight inhibition of grown 9 growth equal to that of untreated control The active compounds, the active compound concentrations and the results can be seen from Table 4.

Table 4

| Active compounds | Mycelium growth test at an active compound concentration of 10 ppm | | | | | | | | | | | | | | | | |
|---|---|---|---|---|---|---|---|---|---|---|---|---|---|---|---|---|---|
| | A | B | C | D | E | F | G | H | I | J | K | L | M | N | O | P | Q |
| 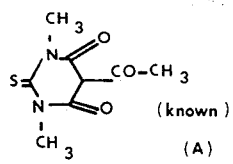 (known) (A) | 9 | 5 | 9 | 9 | 9 | 9 | 9 | 9 | 9 | 5 | 9 | 5 | 9 | 5 | 9 | 9 | 9 |
| (22) | — | 5 | — | — | 3 | 1 | 5 | — | 5 | 1 | — | 1 | — | 1 | — | 1 | — |
| (1)  | 3 | 3 | 3 | — | 1 | 1 | — | 3 | — | 1 | — | 1 | 1 | 1 | 1 | 1 | — |
| (9)  | — | 5 | — | 5 | — | 5 | 5 | — | 1 | — | 1 | — | 1 | — | 1 | — | — |
| (18) | 5 | 3 | 5 | 1 | — | 5 | 5 | 5 | — | 3 | — | 3 | — | 1 | 1 | 3 | — |
| (38) | — | — | — | — | 3 | 1 | — | — | — | — | 1 | — | 1 | 1 | 5 | — | — |
| (35) | — | — | — | — | 5 | 5 | — | — | 3 | — | 5 | — | 1 | 1 | 1 | — | — |
| (59) | — | 1 | 5 | 1 | — | 1 | 5 | 5 | 3 | 1 | — | 3 | 1 | 1 | 1 | 1 | 5 |
| (3)  | — | — | — | 5 | 5 | — | — | 5 | — | 3 | — | 5 | — | 5 | 5 | — | — |
| (23) | — | — | — | — | 5 | — | — | — | — | — | — | 1 | — | 1 | 1 | 1 | — |
| (15) | 1 | 1 | 5 | — | — | 3 | — | 3 | — | 1 | — | 1 | — | 1 | 1 | 1 | — |
| (17) | 5 | 1 | 5 | 5 | — | 3 | 5 | 3 | — | 1 | — | 1 | — | 1 | — | — | — |
| (63) | 3 | 1 | 3 | 1 | 2 | 2 | 3 | 1 | 5 | 2 | — | 1 | 1 | 1 | 1 | — | — |
| (27) | 1 | 1 | 3 | 1 | 3 | 3 | 5 | 3 | 5 | 1 | — | 3 | — | 1 | 1 | 5 | — |
| (31) | 1 | 1 | 3 | 2 | 5 | 3 | 5 | 3 | 5 | 1 | — | 3 | — | 3 | 1 | 3 | — |
| (19) | 1 | 1 | 3 | 2 | 3 | 5 | 3 | 3 | — | 3 | — | 3 | — | — | 1 | 1 | — |
| (10) | — | — | — | — | — | — | 5 | — | 1 | — | — | 3 | — | 5 | — | — | — |
| (42) | 3 | 5 | 3 | 5 | — | 5 | 5 | 5 | 5 | 1 | — | 1 | — | 5 | — | 5 | — |
| (50) | — | — | — | — | 5 | 5 | 5 | — | 5 | — | — | 3 | — | 1 | — | — | — |
| (60) | 3 | — | 5 | 5 | 1 | 5 | 5 | 5 | 5 | 3 | — | 3 | — | — | — | — | — |
| (5)  | 5 | 5 | 5 | 5 | 3 | 5 | 5 | 5 | 5 | 5 | — | 1 | — | 1 | — | 5 | — |
| (11) | — | 5 | — | 5 | 3 | 5 | 3 | 5 | — | — | — | 3 | — | 1 | — | — | — |
| (6)  | 5 | 5 | 5 | 5 | 1 | 5 | 3 | 2 | — | 3 | — | 3 | — | 1 | — | — | — |
| (12) | — | 5 | — | 3 | 3 | 5 | 5 | 5 | 5 | — | 1 | — | 1 | — | 5 | — | — |
| (21) | — | — | — | — | — | — | — | 5 | 1 | 5 | 1 | — | 1 | 1 | 1 | — | — |

A Fusarium culmorum
B Sclerotina sclerotiorum
C Fusarium nivale
D Colletotrichum coffeanum
E Rhizoctonia solani
F Pythium ultimum
G Cochliobolus miyabeanus
H Botrytis cinerea
I Verticillium alboatrum
J Pyricularia oryzae
K Phialophora cinerescens
L Helminthosporium gramineum
M Mycosphaerella musicola
N Phytophthora cactorum
O Venturia inaequalis
P Pellicularia sasakii
Q Xanthomonas oryzae It will be appreciated that the instant specification and examples are set forth by way of illustration and not limitation, and that various modifications and changes may be made without departing from the spirit and scope of the present invention.

What is claimed is:

1. A 2-amidocarbonylthiobarbituric acid of the formula

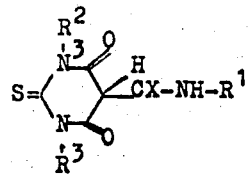

in which
R¹ is alkyl with 1 to 12 carbon atoms, alkoxyalkyl with 1 to 12 carbon atoms in the alkyl moiety and 1 to 3 carbon atoms in the alkoxy moiety, alkylthioalkyl with 1 to 6 carbon atoms in the alkyl moiety and 1 to 3 carbon atoms in the alkylthio moiety, haloalkyl with 1 to 12 carbon atoms in the alkyl moiety and 1 to 3 halogen atoms, cyclopentylmethyl, cyclohexylmethyl, alkenyl with 2 to 6 carbon atoms, cyclopentyl, cyclohexyl, cyclopentenyl, cyclohexenyl, haloalkenyl with 2 to 6 carbon atoms and 1 to 3 halogen atoms, alkylthiocarbonyl or alkoxycarbonyl with 1 to 4 carbon atoms in the alkyl moiety, aryl or aralkyl with 6 to 10 carbon atoms, or aryl or aralkyl with 6 to 10 carbon atoms and substituted with at least one member selected from the group consisting of halogen, haloalkyl or haloalkoxy with 1 or 2 carbon atoms and 2 to 5 halogen atoms, straightchain or branched alkyl with 1 to 4 carbon atoms, alkoxy or alkylthio with 1 to 4 carbon atoms, alkylsulfonyl with 1 to 4 carbon atoms and nitro, $R^2$ and $R^3$ each independently is alkyl with 1 to 6 carbon atoms, alkenyl with 2 to 6 carbon atoms, cyclopentyl, cyclohexyl, phenyl, benzyl or hydrogen, provided that not more than one $R^2$ and $R^3$ is hydrogen, and X is oxygen or sulfur.

2. A compound according to claim 1 which is 5-(3'-chloro-1'-anilido)-carbonyl-1-methyl-3-ethyl-2-thiobarbituric acid of the formula

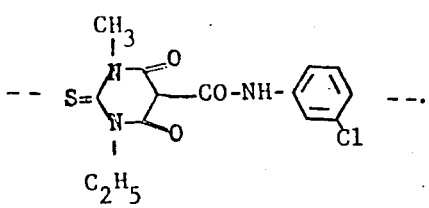

3. A compound according to claim 1 which is 5-(4'-trifluoromethyl-1'-anilido)-carbonyl-1,3-dimethyl-2-thiobarbituric acid of the formula

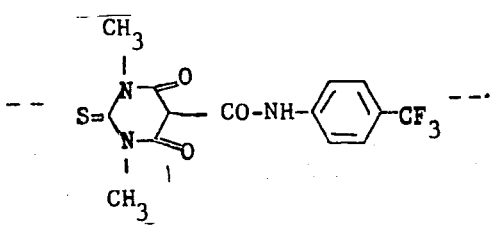

4. A compound according to claim 1 which is 5-(2'-methyl-4'-chloro-1'-anilido)-carbonyl-1-methyl-3-ethyl-2-thiobarbituric acid of the formula

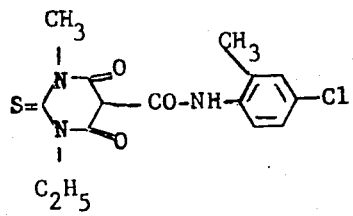

5. A compound according to claim 1 which is 5-(3'-chloro-4'-trifluoromethoxy-1'-anilido)-carbonyl-1,3-dimethyl-2-thiobarbituric acid of the formula

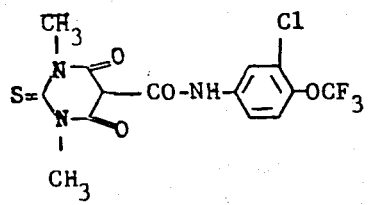

6. A compound according to claim 1 which is 5-(3'-chloro-4'-trifluoromethoxy-1'-anilido)-carbonyl-1-methyl-3-ethyl-2-thiobarbituric acid of the formula

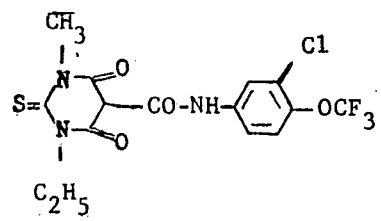

7. A compound according to claim 1 which is 5-(2'-methyl-1'-cyclohexylamido)-carbonyl-1,3-dimethyl-2-thiobarbituric acid of the formula

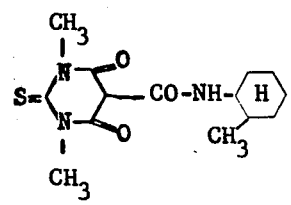

8. An insecticidal, acaricidal, fungicidal, or bactericidal composition containing as active ingredient an insecticidally, acaricidally, fungicidally or bactericidally effective amount of a compound according to claim 1 in admixture with a diluent.

9. A method of combating insects, acarids, fungi, or bacteria which comprises applying to the insects, acarids, fungi, or bacteria or a habitat thereof an insecticidally, acaricidally, fungicidally, or bactericidally effective amount of a compound according to claim 1.

10. The method according to claim 9 in which said compound is 5-(3'-chloro-1'-anilido)-carbonyl-1-methyl-3-ethyl-2-thiobarbituric acid,
5-(4'-trifluoromethyl-1'-anilido)-carbonyl-1,3-dimethyl-2-thiobarbituric acid,
5-(2'-methyl-4'-chloro-1'-anilido)-carbonyl-1-methyl-3-ethyl-2-thiobarbituric acid,
5-(3'-chloro-4'-trifluoromethoxy-1'-anilido)-carbonyl-1,3-dimethyl-2-thiobarbituric acid,
5-(3'-chloro-4'-trifluoromethoxy-1'-anilido)-carbonyl-1-methyl-3-ethyl-2-thiobarbituric acid , or
5-(2'-methyl-1'-cyclohexylamido)-carbonyl-1,3-dimethyl-2-thiobarbituric acid.

* * * * *

UNITED STATES PATENT AND TRADEMARK OFFICE
CERTIFICATE OF CORRECTION

PATENT NO. : 3,961,051
DATED : June 1, 1976
INVENTOR(S) : Wolfgang Kramer et al

It is certified that error appears in the above-identified patent and that said Letters Patent are hereby corrected as shown below.

| | |
|---|---|
| Col. 5, line 9 | Change "Doaralis" to --Doralis-- |
| Col. 5, line 30 | Change "cryssorrhoea" to --chrysorrhoea-- |
| Col. 5, line 43 | Change "Colordao" to --Colorado-- |
| Col. 5, line 65 | Change "Gryrllus" to --Gryllus-- |
| Col. 6, line 9 | Change "hous" to --house-- |
| Col. 7, line 21 | Change "kieselguhur" to --kieselguhr-- |
| Col. 14, Compound 36 | Under $R_3$ column, change "C2H5" to --$C_2H_5$-- |
| Col. 29, line 12 | Triethylammonium Salt Change "0.1" to --0.01--. |
| Col. 31, line 56 | Change "$N^3$" to --N-- under $R^2$ |

Signed and Sealed this

*Thirty-first* Day of *January 1978*

[SEAL]

Attest:

RUTH C. MASON
*Attesting Officer*

LUTRELLE F. PARKER
*Acting Commissioner of Patents and Trademarks*